US008178749B2

(12) United States Patent
Biteau et al.

(10) Patent No.: US 8,178,749 B2
(45) Date of Patent: May 15, 2012

(54) PROCESS FOR THE PRODUCTION OF RECOMBINANT PROTEINS USING CARNIVOROUS PLANTS

(75) Inventors: Flore Biteau, Nancy (FR); Frédéric Bourgaud, Vandoeuvre les Nancy (FR); Eric Gontier, Hebecourt (FR); Jean-Paul Fevre, Orthez (FR)

(73) Assignee: Plant Advanced Technologies PAT SAS, Nancy (FR)

( * ) Notice: Subject to any disclaimer, the term of this patent is extended or adjusted under 35 U.S.C. 154(b) by 503 days.

(21) Appl. No.: 12/444,097

(22) PCT Filed: Aug. 29, 2007

(86) PCT No.: PCT/EP2007/058950
§ 371 (c)(1),
(2), (4) Date: Aug. 10, 2009

(87) PCT Pub. No.: WO2008/040599
PCT Pub. Date: Apr. 10, 2008

(65) Prior Publication Data
US 2010/0047864 A1 Feb. 25, 2010

Related U.S. Application Data

(60) Provisional application No. 60/856,784, filed on Nov. 6, 2006.

(30) Foreign Application Priority Data

Oct. 4, 2006 (FR) .................................... 06 08693

(51) Int. Cl.
*C12N 15/82* (2006.01)
*A01H 5/00* (2006.01)
(52) U.S. Cl. .................. 800/278; 800/288; 800/298
(58) Field of Classification Search ........................ None
See application file for complete search history.

(56) References Cited

FOREIGN PATENT DOCUMENTS

| EP | 0019808 B1 | | 12/1980 |
|---|---|---|---|
| WO | WO 99/16890 | * | 4/1999 |
| WO | WO 99/38990 | | 8/1999 |
| WO | WO 99/42115 | | 8/1999 |
| WO | WO 02/057408 A2 | | 7/2002 |
| WO | WO 2004/011657 A1 | | 2/2004 |

OTHER PUBLICATIONS

Haseloff et al. Removal of a crytpic intron and subcellular localization of green fluorescent protein are required to mark transgenic *Arabidopsis* plants brightly. (1997) PNAS USA; vol. 94; pp. 2122-2127.*
International Search Report issued in application No. PCT/EP2007/058950 on Nov. 21, 2007.

Burch-Smith, T.M., et al., "Applications and advantages of virus-induced gene silencing for gene function studies in plants," The Plant Journal, 2004, pp. 734-746, vol. 39.
Chikwamba, R.K., et al., "Localization of a bacterial protein in starch granules of transgenic maize kernels," PNAS, 2003, pp. 11127-11132, vol. 100, No. 19.
De Block, M., The cell biology of plant transformation: Current state, problems, prospects and the implications for the plant breeding, Euphytica, 1993, pp. 1-14, vol. 71.
Frazier, C.K., "The Enduring Controversies Concerning the Process of Protein Digestion in *Nepenthes* (*Nepenthaceae*)," Department of Biology, 2000, pp. 1-8, University of New Mexico, Albuquerque, NM 87131 USA, @International Carnivorous Plant Society.
Yuan, G., et al., "Expression of Human BMP-2 Gene in Different Tissues of Tobacco Plants," Acta Genetica Sinica, 2006, pp. 56-62, vol. 33, No. 1.
Juniper, "Chapter 3—The Habitats of Carnivorous Plants and their Regional Distribution," 1989, pp. 21-25.
Lobareva, L.S., et al., "Pepsin-Like Protease From Insectivorous Plant *Nepenthes*," Chemical Faculty, State University of Moscow, 1973, pp. 640-642.
Matušikov'A, I., et al., "Tentacles of in vitro-grown round-leaf sundew (*Drosera rotundifolia* L.) show induction of chitinase activity upon mimicking the presence of prey," Planta, 2005, pp. 1020-1027, vol. 222.
Nicchitta, C.V., "A platform for compartmentalized protein synthesis: protein translation and translocation in the ER," Current Opinion in Cell Biology, 2002, pp. 412-416.
Pratelli, R., et al., "A new catch in the SNARE," Trends in Plant Science, 2004, pp. 187-195, vol. 9, No. 4.
Schweikert, R.J., et al., "Poster: Protein targeting and vesicular trafficking," Abs. P20037, 2006, http://www.conncoll.edu.
Takahashi, K., et al., "Specific Inhibition of Acid Proteases from Brain, Kidney, Skeletal Muscle, and Insectivorous Plants by Diazoacetyl-DL-norleucine Methyl Ester and by Pepstatin," J. Biochem., 1974, pp. 897-899, vol. 76, No. 4.
Ullah, A.H.J., et al., Fungal *phyA* gene expressed in potato leaves produces active and stable phytase, Biochemical and Biophysical Research Communications, 2003, pp. 603-609, vol. 306.
Voinnet, O., "Induction and Suppression of RNA Silencing: Insights From Viral Infections," Nature, 2005, pp. 206-221, vol. 6.
An, C., et al., Aspartic proteinases are expressed in pitchers of the carnivorous plant *Nepenthes alata* Blanco., Planta, 2002, pp. 661-667, vol. 214 [XP-002453529].
Athauda, S.B.P., et al., "Enzymic and structural characterization of nepenthesin, a unique member of a novel subfamily of aspartic proteinases," Biochem. J., 2004, pp. 295-306, vol. 381, [XP-002453530].
Kitko, R.D., et al.,"*Drosera capensis* (*Droseraceae*) a Model Carnivorous Plant," Database accession No. PREV200400439018 abstract & Journal of the Pennsylvania Academy of Science, vol. 77, Mar. 2004, p. 137.

(Continued)

*Primary Examiner* — Cathy Kingdon Worley
(74) *Attorney, Agent, or Firm* — Foley & Lardner LLP (57) ABSTRACT

The present application relates to the provision of process for producing at least one protein, comprising the cultivation of a carnivorous plant, characterized in that said plant has been genetically modified to express said protein or proteins, and said protein or proteins are collected from the digestive secretions of said carnivorous plant traps, in particular glue, pitcher, trumpet or bladder traps. The proteins of interest are functional, despite the existence of digestive enzymes.

23 Claims, 7 Drawing Sheets

OTHER PUBLICATIONS

Gallie, D., et al., "Signal Transduction in the Carnivorous Plant *Sarracenia purpurea*," Plant Physiol., vol. 115, pp. 1461-1471, 1997.

Hirsikorpi, M., et al., *Agrobacterium*-mediated transformation of round leaved sundew (*Drosera rotundifolia* L.), Plant Science, 2002, pp. 537-542, vol. 162.

Kämäräinen, T., et al., "Production of 7-Methyljuglone in *Drosera rotundifolia* In Vitro and Ex Vitro," Department of biology Botany and Department of Chemistry, University of Oulu, Finland, 2003, pp. 1-4, [XP008077528].

Pratelli, R., et al., "A new catch in the SNARE," Trends in Plant Science, 2004, pp. 187-195, vol. 9, No. 4 [XP-002428634].

Schulze, W. et al., "Transporters for ammonium, amino acids and peptides are expressed in pitchers of the carnivorous plant *Nepenthes*," The Plant Journal, 1999, pp. 637-646, vol. 17, No. 6 [XP-002418467].

Kämäräinen, T., et al., "Production of 7-Methyljuglone in *Drosera rotundifolia* In Vitro and Ex Vitro," Proceedings of the First International Symposium on Acclimatization and Establishment of Micropropagated Plants, Acta Horticulturae No. 616, 2003, pp. 507-510, [XP-008077528].

\* cited by examiner

PROCESS FOR THE PRODUCTION OF RECOMBINANT PROTEINS USING CARNIVOROUS PLANTS

This invention concerns a process for producing at least one protein, comprising the cultivation of a carnivorous or insectivorous plant, characterized in that said plant has been genetically modified to express said protein or proteins.

Today, proteins represent a category of molecules that is widely used both in the therapeutic or diagnostic fields and as laboratory reagents. Thus there have been many efforts made to improve existing recombinant protein production processes or to develop new more effective systems of production.

The usual systems for producing recombinant proteins involve different types of living organisms which can be genetically modified: microorganisms (bacteria, yeasts, fungi), cultured mammalian cells, cultured insect cells, transgenic animals or transgenic plants.

Transgenic plant systems offer advantages. In particular, they provide greater biological safety, as no known pathogenic agents can infect both plants and animals. In addition, large-scale production is possible by cultivating these transgenic plants. It can also be less costly than other systems of industrial production. Using transgenic plants also allows proteins to be produced which have undergone one or more post-translational maturation processes. Finally, with current plant biotechnology, tissues in which the protein of interest will accumulate, such as the leaves or the seeds, which are readily accessible, can be specifically targeted.

The expression of the recombinant protein is generally directed to the leaves and seeds. Leaves provide many possibilities for synthesis (1). Thus, for example, genetically modified tobacco is used for the production of human hemoglobin. However, sometimes leaves contain unwanted substances which are difficult to eliminate (polyphenols present in tobacco leaves). In addition, recombinant proteins must be quickly extracted from these leaves because they rapidly deteriorate.

Seeds are also sometimes used as storage tissue, because of the greater stability of the environment in which the proteins accumulate with its low water content. Thus, for example, genetically modified maize is used for the production of gastric lipase. Seeds have limitations mainly due to a lower synthetic capacity, and the necessity to wait for flowering with an increased risk of the transgene being dispersed by cross-pollination.

In both cases, the main drawback of these systems of producing recombinant proteins in the leaves or seeds of transgenic plants is linked to the fact that demanding extraction/purification stages are required for separating the recombinant protein from the plant tissues, whether leaves or seeds. Indeed, the recombinant protein is inserted into the plant tissue matrix, which makes it difficult to extract and purify, while this step must be carried out as quickly as possible due to the rapid proteolysis which follows homogenization (2). This last step limits the advantages therefore of current systems for producing recombinant proteins using transgenic plants. Consequently there is a real need for systems of production which retain the advantages of the current production systems using transgenic plants yet limit their disadvantages as far as possible, particularly by considerably simplifying the extraction/purification of the recombinant protein.

Carnivorous plants are plants capable of capturing prey and assimilating all or part of it to obtain a proportion of their nitrogen requirements. In addition to their ability to fix carbon dioxide from the air for their photosynthetic needs, and to absorb water and mineral salts via their roots, these plants, which often live in environments lacking nutrients, have developed traps on their leaves of different types, functioning in various ways to capture the prey that provides them with additional nitrogen. Despite their varied forms and ways of functioning, the traps of carnivorous plants have the common feature of producing liquids containing digestive enzymes that permit more or less efficient digestion of the prey and its assimilation.

In carnivorous plants there is a system expressing and transporting digestive enzymes into the traps, where these enzymes, which are in a more or less viscous and sticky liquid, are directly accessible and easy to purify. In addition, collecting digestive juices from the traps can be carried out without destroying the plant, which can therefore continue producing. In certain genera, and subject to certain precautions, collecting the digestive juices may be carried out under sterile conditions, even when the plant is cultivated in a non-sterile environment. Finally, the excretion of digestive juices in the traps may be induced by a chemical or even a mechanical stimulus due to the presence of a trapped insect. The chemical stimulus can be replaced by applying a solution containing organic nitrogen, phosphate, sodium chloride, gelatin, salicylic acid, or chitin (3; 4), thus potentially easily increasing production of purified proteins from the digestive juices.

Various documents therefore describe the purification of carnivorous plant proteins. Application EPOO19808 (5) describes using digestive juices of carnivorous plants in the treatment of cancer. In the same way, application WO9942115 (6) describes using the digestive juices of carnivorous plants to inhibit kinase proteins involved in certain diseases. Patent application WO02057408 (7) describes employing chitinases, proteins found in the natural state in the leaf juices of carnivorous plants of the *Nepenthes* genus, for pharmaceutical use (anti-fungal) or agricultural use (anti-cryptogamic diseases). Nevertheless, in each of these documents, the proteins produced and purified are native endogenous proteins of the carnivorous plant. As the carnivorous plants have not been genetically modified, no recombinant protein is produced. At no time do these patents mention the possibility of producing proteins from carnivorous plants other than those already present in these plants under natural conditions.

Moreover, an article by Hirsikorpi et al. describes the transformation of *Drosera rotundifolia* by the vector *Agrobacterium* with a luciferase gene (8). Nevertheless, at no time did any result show the presence of the luciferase protein in the juices found on the surface of the leaves of the plant.

Indeed, only certain proteins are transported into the digestive juices of carnivorous plants. The process of protein excretion by carnivorous plants has been the subject of several anatomical descriptions (9). Although there is no formal proof, it seems true to say that the production of leaf secretions is due to increased production of Golgi vesicles from the endoplasmic reticulum (ER), as is already the case in other plants (10). Nevertheless, the presence of a protein within the ER provides no guarantee that it will be excreted by the plant.

In general, recent publications have sometimes described unexpected results in terms of the location of proteins. Nothing guarantees therefore that a protein, without any addressing signal or even with an addressing signal to the ER, will be excreted in sufficient quantity to be detected in the digestive secretions of the traps of carnivorous plants. For this reason, only proteins already naturally present in the digestive secretions of carnivorous plant traps have until now been purified.

No document has described or suggested the possibility of generating a genetically modified carnivorous plant excreting a recombinant protein into its traps.

In addition, the digestive juices secreted into carnivorous plant traps contain digestive enzymes, such as proteases, peroxidases, ribonucleases, lipases, amylases, esterases, acid phosphatases, chitinases and glycosylases. This natural capacity to secrete digestive enzymes, particularly proteases, into the traps a priori forms an obstacle to producing recombinant proteins by secretion into the traps due to the risk of degradation induced by the presence of these proteases.

Nevertheless, the inventors have surprisingly found that it is possible to generate genetically modified carnivorous plants expressing an exogenous recombinant protein, a significant quantity of which is detectable in the digestive secretions in the traps. In addition, tests carried out by the inventors on several distinct recombinant proteins have shown that it is possible to isolate functional proteins which are not therefore significantly degraded by the digestive enzymes. The inventors have shown that, contrary to expectations, by genetically modifying a carnivorous plant for it to express a recombinant exogenous protein, it is possible to detect this recombinant protein in sufficient quantity in the digestive secretions of the plants and to purify this protein in a functional form, despite the existence of digestive enzymes. Now that problems concerning the transport of the recombinant protein into the traps and the breakdown by the digestive enzymes have been overcome, this system of production presents numerous advantages relating to collecting the recombinant protein from the digestive secretions of traps:

The plant is neither destroyed nor significantly harmed by the collection and can therefore be kept growing for other later collections;

The traps are naturally readily accessible organs, allowing easy collection of the digestive secretions;

In some carnivorous plants, particularly those with traps in the form of pitchers or bladders, a certain quantity of digestive secretions are produced and excreted into traps which are closed to the external environment; the trap only opens to the external environment once it is ready to digest prey. Even if the plant is grown in a non-sterile environment, during the trap preparation period, the digestive juices are excreted under naturally sterile conditions. Subject to collecting the digestive secretions before the trap opens and taking a few precautions, the collection of recombinant proteins can, in certain production methods, be made under sterile conditions.

The fact that the recombinant protein to be purified is present in a liquid medium outside the plant, and not in a solid plant tissue (such as a leaf or seed), greatly simplifies the stage of purifying the recombinant protein;

Finally, this system may be induced in that the excretion of digestive juices can be increased by mechanical and/or chemical signals mimicking the presence of a prey.

The invention concerns a process for producing at least one protein, comprising the cultivation of a carnivorous plant, characterized in that said plant has been genetically modified to express said protein or proteins.

In a preferred embodiment, said process is further characterized in that said protein or proteins are collected from the digestive secretions of said carnivorous plant traps.

The term "carnivorous plant" means any plant capable of capturing and digesting animal prey, any type of prey from the animal kingdom being included in this definition, using a system of expression and transport of digestive enzymes into traps. Usually, the animal prey are insects (and the plants are referred to more precisely as insectivorous plants), but small rodents or batrachians, or even small aquatic animals in the case of aquatic carnivorous plants, can also be caught in the traps of certain carnivorous plants. The term "carnivorous plant" used here therefore includes all types of carnivorous plants that have a system of expression and transport of digestive enzymes into traps, and in particular, though not exclusively, insectivorous plants. On the other hand, only carnivorous plants with a system of expression and transport of digestive enzymes into traps are included in the meaning of the invention. In particular, certain genera of plants in which the absence of secretion of digestive enzymes is compensated by the presence of microorganisms external to the plant secreting digestive enzymes, although usually considered among carnivorous plants, are not considered as carnivorous plants in the meaning of this invention. Thus, the genera *Brochinia, Catopsis berteroniana, Ibicella lutea, Heliamphora*, and *Darlingtonia* are not considered as being carnivorous plants in the meaning of the invention.

As previously indicated, carnivorous plants are of interest because of the existence of proteins excreted in the digestive juices of the traps. The proteins are directly accessible, easy to purify, since they are not inserted into plant tissue, and at least in certain cases and for a certain time, are stored in a sterile form by the plant.

To benefit from these advantages, the recombinant protein expressed by the plant must also be excreted into the plant's traps. Thus, in a process according to the invention, said protein or proteins are advantageously expressed in the plant cells and excreted by the native system excreting the natural proteins of said plant.

Thus, the recombinant protein or proteins expressed by the genetically modified carnivorous plant can be easily collected from the digestive secretions of said plant traps.

The term "genetically modified plant" means a plant into which a gene or a fragment of a gene has been inserted. This therefore includes plants which have been transformed with an expression vector of the gene or gene fragment of interest, allowing the expression of this gene or gene fragment in this plant. The gene of interest, which is totally or in part inserted in the plant, may be an exogenic gene, not naturally expressed by the plant, or an endogenous gene already naturally expressed by the plant but of which it is wished to increase that expression.

In particular, in an advantageous embodiment of a process according to the invention, the carnivorous plant which is cultivated has been genetically modified by *Agrobacterium*, biolistics, electroporation or microinjection transformation or by the use of viral vectors.

The transformation of plants using *Agrobacterium* is a technology well known to those in the field. Briefly, *Agrobacterium tumefaciens*, a pathogenic microorganism in plants, has been known since the beginning of the $20^{th}$ century. *A. tumefaciens* has the exceptional natural capacity of transferring a particular segment of DNA (T-DNA) from its tumor inducing plasmid (Ti) to the nuclei of infected plant cells where it is then integrated in a stable fashion into the host genome and transcribed, causing crown gall disease. The fragment of T-DNA is flanked by direct repetitions of 25 base pairs (bp) acting as cis-regulatory element signals for the transfer apparatus. It has been demonstrated that in reality, all foreign DNA placed between these T-DNA borders can be transferred to plant cells. It is therefore possible to generate strains of *Agrobacterium* in which the genes causing the disease have been replaced by a DNA selected in a specific way, thus allowing this specifically selected DNA to be integrated in a stable manner into the genome of the plant.

Biolistic transformation of plants, still called particle bombardment, is a technology used to release DNA directly into the host genome which is just as well known to those working in the field.

To summarize, a plasmid or linearized DNA containing the gene or genes concerned is fixed to tungsten or gold particles (microbeads) which are released into the host cells at high speed so as to penetrate the plant cell nuclei. In the nucleus, the DNA can separate from the carrier microbead and incorporate itself into the host's genome. Particle bombardment or biolistics can be used for transforming the tissue of most plant species.

The technology of electroporation of protoplasts, well known to those working in the field, which uses electrical impulses, can also be used to transform a plant. Briefly, it consists of subjecting a mixture of protoplasts and DNA to a series of short high voltage electric shocks. The electric field causes destabilization of the plasma membrane by polarization of the phospholipids forming it and thus induces the formation of pores through which the DNA molecules can pass. If the electric shock has not been too violent, the phenomenon is reversible and the membrane returns to its initial state, leaving the protoplast perfectly viable.

The microinjection technology consists of directly injecting selected DNA, using micropipettes or microsyringes under the microscope, into the nuclei of protoplasts.

Viral vectors can also be used for transformation. This technology, well known to those working in the field, consists of using a plant virus with double-stranded DNA in the genome of which the pathogenic genes have been inactivated and the gene of interest inserted. The plant is thus transformed by infection with the modified virus.

Transformation has been carried out advantageously with *Agrobacterium tumefaciens*, by biolistics and by electroporation, the commonest technologies in use.

The term "protein" is considered to mean any type of polymer containing an skeleton of amino acids. This term therefore includes not only complete proteins but also peptides or polypeptides corresponding to sub-units or fragments of complete proteins and any peptide or polypeptide of interest, even where it does not correspond to a fragment of a known protein, whether it is a variant of such a fragment (with mutations relative to the reference fragment) or a created peptide or polypeptide. In particular, in the meaning of the invention, a protein can include modified amino acids which do not exist in the natural state. In the same way, peptide bonds may have been modified. In addition, the term protein in the meaning of the invention also includes the facultative presence of post-translational modifications by glycosylation, phosphorylation or methylation.

In addition, said protein produced by a process according to the invention may have an interest in any field of human activity. Particularly, said protein may be selected from a medicinal product for veterinary or human use, a cosmetic agent, a phytopharmaceutical agent, a diagnostic agent, a nutraceutical agent or a laboratory reagent.

The term "medicinal" protein means any protein which is subject to marketing authorisation for treating human or veterinary diseases. Such medicinal proteins include particularly protein hormones (sex hormones, growth hormones etc.), enzymes, antibodies (in particular monoclonal antibodies) etc.

The term "cosmetic agent" protein means any protein allowing the external parts of the human body to be cleansed, kept in good condition or embellished, particularly the skin or the hair. Examples of cosmetic agent proteins include collagen, botulinum toxin and snake venom proteins used in skin care.

The term "phytopharmaceutical agent" protein means any protein protecting plants or plant products against any harmful organisms, or preventing their action, which particularly includes pesticides; any protein acting on the vital processes of plants, e.g. by increasing or decreasing their growth; or any protein which preserves plant products.

The term "diagnostic agent" protein means any protein involved in an in vitro or in vivo test determining the presence or absence of a particular disease or condition in a subject. Such diagnostic agent proteins include in particular:
  antibodies against a protein the occurrence of which in a sample indicates the presence of a disease, such as, for example, antibodies against the antigens of pathogenic microorganisms or tumor antigens, thus permitting microorganisms or a cancer to be detected;
  proteins specifically expressed in the event of disease, such as, for example, the proteins of pathogenic microorganisms, thus allowing detection in a subject of the presence of antibodies against these proteins and therefore diagnosis of the disease.

The term "laboratory reagent" protein means any protein used in medical laboratory analysis or research, such as, particularly, an antibody, an enzyme, an antigen, a hormone, a cytokine, a chemokine, a cellular receptor etc.

The term "nutraceutical protein" means any protein used for its alleged health benefits, to maintain the healthy condition of the consumer, such as in particular proteins acting on cellular regeneration or proliferation, on the central nervous system, the cardiovascular system, allergies, and the prevention of metabolic diseases (obesity, diabetes).

Cultivation of the carnivorous plant used in a process according to the invention is carried out in a conventional manner, taking into account the special features of the selected type of carnivorous plant. The methods of cultivation of the different types of carnivorous plants are well known to those working in the field. In general many carnivorous plants grow in soils which are very rich in organic matter (e.g. peat bogs), or even as lianas growing on host trees (this is the case for *Nepenthes*). Some are aquatic such as the utricularias. General protocols for the cultivation of carnivorous plants are described in the book by Juniper et al (11), which can then be readily adapted by those working in the field to each particular plant.

One of the previously mentioned advantages related to using the carnivorous plant's natural system for excreting proteins is that the system can be induced by mechanical and/or chemical signals mimicking the presence of a prey. Thus, in an advantageous embodiment of the process according to the invention, the plant is subjected to chemical and optionally mechanical stimuli, mimicking the capture of a prey and inducing activation of the system producing proteins by said plant and excreting them into the traps. Such chemical stimuli can notably include the application of a solution containing organic nitrogen, phosphate, sodium chloride, gelatin, salicylic acid, or chitin (1,2). Nevertheless, the plant may also be cultivated in the absence of any chemical and/or mechanical stimulus mimicking the capture of a prey and inducing activation of the system producing proteins by said plant and excreting them into traps.

As previously indicated, one of the problems potentially connected with the excretion of the recombinant protein of interest in the traps' digestive secretions is related to the presence of digestive enzymes in these secretions, particularly proteases. Apart from the fact that the inventors have shown that the presence of these digestive enzymes is not in reality a obstacle to purifying functional proteins, in order to reduce still further the risks related to these enzymes it is also possible to include in the process according to the invention inhibition of the synthesis of one or more digestive enzymes by said carnivorous plant, and in particular of one or more proteases. Thus, according to one embodiment of the process according to the invention, said process further comprises the inhibition of the synthesis of one or more digestive enzymes by said carnivorous plant. Advantageously, at least one of said digestive enzymes the synthesis of which is inhibited is a protease. Indeed, these are the most likely enzymes to damage the recombinant protein excreted in the traps. Nevertheless, other proteins which could degrade the recombinant protein could also be targeted. For example, in the case of a glycosylated protein, it is possible to target, alone or at the same time as the proteases, one or more glycosylases. Other enzymes which could damage other types of post-translational modifications could also be targeted.

Such inhibition may be partial or total and may be induced in different ways.

Firstly, it may be induced using genetic technologies producing such an inhibition.

In particular, it is possible to directly target genes the expression of which one wishes to inhibit, notably by deleting the gene or genes of the digestive enzyme from the genome of the plant or by turning off the transcription of these genes, a process known as "gene silencing".

Deletion from the genome of the plant of the gene or genes of the targeted digestive enzyme or enzymes, also known as "knock-out" or "KO", is performed using technologies now well known to those working in the field.

Switching off the transcription of the gene or genes of the targeted digestive enzyme or enzymes by silencing encompasses a series of technologies which are well described for plants.

Thus the Virus Induced Gene Silencing technology (VIGS) requires cloning of a short sequence of the targeted plant gene in a plant virus. During the few weeks following the viral infection containing the gene fragment in question, the natural defense mechanism of the plant specifically breaks down the mRNA corresponding to the targeted endogenous gene of the plant. With this technology and starting from a normal plant, the targeted gene is rapidly silenced within 3 to 4 weeks of the viral infection, using the principle of systemic contamination of the plant with the virus, without in vitro regeneration of transformants (12).

Co-deletion can also specifically switch off the expression of targeted genes. This switching off is achieved by reinserting a target gene, under the control of a constitutive or inducible or tissue specific promoter in a given plant. Gene transfer can use any genetic transformation technology (Agrobacterium infection, viral vector, microinjection, biolistics etc.). In some genetically transformed plants, disappearance of the character or function coded by the target gene can be seen (13).

Post-transcriptional inactivation of genes may also be achieved by any plant genetic transformation technology (Agrobacterium infection, viral vector, microinjection, biolistics etc.) by inserting into the target plant a fragment of the gene, the transcription of which is to be switched off, using the principle of interfering RNA (RNAi (14)).

Genetic inhibition of the gene or genes for a targeted digestive enzyme or enzymes may also be carried out indirectly by ectopic expression in the carnivorous plant of at least one protease inhibitor gene, i.e. of at least one gene the expression of which leads to the partial or total reduction in the expression of at least one protease. Thus, in one particular embodiment, the carnivorous plant used is also transformed to express at least one protease inhibitor gene, the transformation being carried out by any technology known to those working in the field, and particularly by any technology described previously. Any type of protease inhibitor gene can be used. Most proteases have an optimal enzyme activity in acid pH. As an example, the two proteases known in plants of the *Nepenthes* genus (an endopeptidase and nepenthesin) are enzymes with optimal activity in acid pH (15). For this reason, it may be useful to use a gene known to inhibit the expression of acid proteases. In particular, the yeast gene IPA3_YEAST (Swissprot accession number P01094), which codes for the inhibitor of saccharopepsin, is known to code for an inhibitor of acid protease close of those in plants of the *Nepenthes* genus.

Thus, in a particular embodiment of a process according to the invention in which the expression of at least one protease is inhibited, the inhibition of the synthesis of one or more proteases by said carnivorous plant is carried out by genetic technologies selected from the deletion from the plant's genome of at least one protease gene, switching off the transcription of at least one protease gene by silencing, and/or ectopic expression of at least one protease inhibitor gene.

Alternatively, inhibition of the synthesis of one or more digestive enzymes by the carnivorous plant may be induced using non-genetic technologies. In particular, the inhibition may also be induced by directly adding a solution inhibiting the targeted digestive enzyme or enzymes to the digestive liquid in the traps, or even by controlling the pH and/or temperature conditions of the digestive liquid so as to limit the activity of the targeted digestive enzyme or enzymes. Indeed, inhibitors are known in the field for most enzymes, and most enzymes have optimal pH and/or temperature conditions beyond which their activity is limited. It is thus possible to limit a target enzyme's activity by putting the digestive secretions in the presence of inhibitors and/or outside of the range of optimal conditions for its enzyme activity.

Indeed, as the traps are readily accessible, it is possible to add to the digestive liquid in the traps a solution containing inhibitors of the targeted digestive enzyme or enzymes, either by injecting the solution into the pitchers or bladders of plants with pitcher traps (e.g. *Nepenthes*) or bladder traps (e.g. *Utricularia*), or by spraying the solution onto the glue of plants with glue traps (e.g. plants in the *Drosera* genus).

As regards more particularly the proteases, different types of protease inhibitors can be used. In particular, it has been shown that the activity of *Nepenthes* proteases were inhibited by an acid protease inhibitor found in animals and fungi: DDE (dichlorodiphenyldichloroethylene, (16)). Two other acid protease inhibitors, DAN (diazoacetyl-DL-norleucine methyl ester) and Pepstatin (3S, 4S-4-amino-3-hydroxy-6-methyl-heptanoic acid) isolated from *Streptomycin testaceus* and other actinomycetes which form a complex with aspartic acid proteases, completely inhibit the digestive activity of *Nepenthes* pitchers (also called ascidia) (15, 17).

Other protease inhibitors and even mixtures of several protease inhibitors targeting different proteins are commercially available. These mixtures inhibit a number of different proteases (e.g. cysteine protease, serine protease, and metalloproteases, and also pepstatin) and provide better protection for preserving our protein of interest.

One or more of these inhibitors can therefore be added in the form of a solution injected into or sprayed onto the traps.

It is also possible to limit the activity of trap proteases by controlling the temperature and/or the pH of the digestive liquids. Indeed, it has particularly been shown that the digestive activity of proteases extracted from the digestive liquid of *Nepenthes* pitchers increases with the temperature to reach an optimum at around 50° C./60° C. (15). It is therefore possible to limit their activity by keeping the plants at a lower temperature from the time when the pitchers are developing. Advantageously, in order to limit protease activity, the temperature should be between 5 and 25° C., would be better between 5 and 20° C., better still between 5 and 15° C., and preferably between 5 and 10° C.

In addition, it has been shown that the protease activity of the digestive fluid of carnivorous plants is optimal at low pH (15), as acidification of the fluid increases digestive activity. It seems that digestion is due mainly to enzymes secreted by the glands when the ascidia are young and the pH low. However, with ageing, the pH increases and microorganisms become responsible for the greater part of digestion. In *Nepenthes villosa*, for example, the digestive fluid remains active for about 4 to 5 months, during which time the pH is maintained at about 2. After this time, the pH rises rapidly to 6. It is therefore possible to take advantage of this by controlling the pH of the digestive fluid, particularly by adding a basic solution, injecting it into the pitchers or bladders or spraying it onto glue traps. This limits the protease activity. As protease activity is optimal at around pH 2-3, the pH should be maintained above 4 or 4.5, more advantageously above 5 or 5.5, with greater advantage still above 6 or 6.5 and preferably above 7 or 7.5. Preferably the pH should not be too basic either and therefore should remain below 9, with advantage below 8.5, preferably below 8. Thus, to control protease activity, the pH should be between 4 and 9, should advantageously be between 5 and 8.5, would more advantageously be between 6 and 8, and preferably between 7 and 8.

Another possible improvement of the process according to the invention consists in enhancing the excretion of the recombinant protein into the traps either by the presence in the protein of a peptide signal sequence permitting its transport into the endoplasmic reticulum (ER) or by enhancing transport from the ER to the Golgi apparatus, then from the Golgi apparatus to the plasma membrane and the traps via the transmembrane route, over-expressing a gene of the SNARE (soluble N-ethylmaleimide sensitive fusion protein attachment protein receptors) family of proteins in the plant.

As regards the peptide signal sequence, as previously indicated, although the presence of such a peptide is not necessarily sufficient to allow export to the traps' digestive fluids, it seems that the excretory route of digestive enzymes present in the traps passes through the ER, and the presence of a peptide signal sequence to the endoplasmic reticulum may thus contribute to better transport of the recombinant protein to the traps. Thus, in one embodiment of the process according to the invention, the protein of interest to be produced comprises a peptide signal sequence allowing its transport into the endoplasmic reticulum. Such a signal sequence may be either present naturally in the protein or fused to a protein which does not have a peptide signal sequence.

Protein addressing into the endomembrane compartment of the ER is determined by two alternative mechanisms:

1/the presence of a signal sequence on the N-terminal part of the protein which may be soluble or later bound to a membrane. This signal sequence generally includes a hydrophobic motif allowing the protein to enter the ER. Following entry into the ER, the protein may be managed by chaperones which ensure the optimal spatial conformation of the protein.
2/the translation of the mRNA into protein which may occur (totally or in part) near the ER, with the assistance of membrane bound ribosomes. Thus for certain proteins, there is a hydrophobic signal sequence of several tens of amino acids in the N-terminal part. During the translation process, a cytoplasmic SRP (signal recognition protein) binds to the surface of the ribosome, which stops the translation process. The SRP particle bound to the ribosome attaches itself to a receptor on the surface of the membranes of the reticulum. The hydrophobic signal sequence of the protein thus crosses the membrane of the ER. Translation starts again and the protein is then released inside the lumen (19).

Thus, for a protein of given interest, it is possible to enhance its addressing to the ER by adding to the primary sequence a peptide signal sequence with hydrophobic properties in the N-terminal position. An example of a hydrophobic N-terminal motif may be found in the family of eukaryote P450 cytochromes, which are enzymes located on the ER membranes (CYP2C5, CYP73A1).

As regards addressing from the ER to the Golgi apparatus and then from the Golgi apparatus to the exterior of the traps, it seems that peptide motifs attached to the vesicles or membranes, known as SNARE (soluble N-ethylmaleimide sensitive fusion protein attachment protein receptors) are involved in the exocytosis process in plants by membrane fusion mechanisms preceded by SNARE-SNARE type molecular interactions (18). In particular, such SNARE peptide motifs targeting the transport of vesicles containing proteins from the ER to the Golgi apparatus have been described in proteins in *Arabidopsis* (18): they are the SNARE domains of Syntaxin-41, Syntaxin-42, Syntaxin-43 peptides (AtSYP41 to 43, respectively Genbank accession numbers: O65359, Q9SWH4, and Q9SUJ1). Other SNARE type peptides are also known in *Arabidopsis*. They are present on the surface of Golgi vesicles and determine transport from the Golgi apparatus to the plasma membrane (exocytosis); they correspond to Syntaxin-121 to 125 (AtSYP121 to 125, Genbank accession numbers: Q9ZSD4, Q9SVC2, Q9ZQZ8, O64791, et Q9SXB0). The various SNARE domains are summarised in table 1 below.

TABLE 1

SNARE domains known for *Arabidopsis thaliana*.

| Gene | Genbank accession number | Region corresponding to the (Amino Acid) SNARE domain |
|---|---|---|
| Syntaxin-41 | O65359 (GI: 28380151) | 237-293 |
| Syntaxin-42 | Q9SWH4 (GI: 28380167) | 232-289 |
| Syntaxin-43 | Q9SUJ1 (GI: 38503420) | 246-302 |
| Syntaxin-121 | Q9ZSD4 (GI: 28380149) | 217-276 |
| Syntaxin-122 | Q9SVC2 (GI: 28380140) | 216-275 |
| Syntaxin-123 | Q9ZQZ8 (GI: 28380148) | 209-268 |
| Syntaxin-124 | O64791 (GI: 28380117) | 206-265 |
| Syntaxin-125 | Q9SXB0 (GI: 28380142) | 201-260 |

Thus a genetically transformed carnivorous plant over-expressing at least one of these two families of SNARE proteins, or a protein having one or more SNARE domains or derivatives, should lead to an increased excretion of the proteins present in its ER. In one embodiment of the process according to the invention, the cultivated carnivorous plant is in addition genetically modified to express at least one gene including at least one SNARE type domain, thus leading to increased excretion of the protein or proteins of interest into the traps. "SNARE type domain" means any peptide motif that is at least 80%, at least 85%, at least 90%, at least 95%, at least 96%, at least 97%, at least 98%, at least 99%, even 100% identical to one of the SNARE domains set out in table 1. In particular, genes including a SNARE domain described in table 1 can be over-expressed in the carnivorous plant used.

The process according to the invention may be used with any type of carnivorous plant. Carnivorous plants can be classified into different categories depending on their type of trap, and the practical aspects of the process according to the invention may therefore vary depending on the type of trap. Various particular advantageous embodiments of the process corresponding to the distinct types of traps are described below.

In particular, depending on the type of carnivorous plant used, or more precisely on the type of traps harbored by the selected carnivorous plant, the collection step of traps digestive secretions is performed using various suitable methods. Several collection methods suitable for a particular trap type, are described below.

However, other embodiments may easily be developed by those working in the field, and the process according to the invention cannot therefore be limited to the particular advantageous embodiments described below.

A first category of carnivorous plants which can be used in an advantageous embodiment of the process according to the invention is that of carnivorous plants possessing glue traps.

The term "glue traps" is intended to mean traps formed by adhesive leaves. These leaves secrete small droplets called glue or mucilage to which the prey become stuck. These traps can be passive (the leaves secreting the droplets of mucilage are immobile) or semi-active (the leaves secreting the mucilage droplets roll up to increase the contact surface, thus allowing better digestion). Several carnivorous plant genera have glue traps. Thus, in the process according to the invention using a carnivorous plant with glue traps, the plant is selected from the *Drosera, Pinguicula, Byblis, Drosophyllum*, and *Triphyophyllum* genera. Advantageously, said carnivorous plant with glue traps belongs to the *Drosera* genus.

In these carnivorous plants with glue traps, the mucilage is directly accessible to the open air, and the protein of interest can be obtained directly by harvesting the glue present in the open air. Harvesting the glue from the traps may thus be carried out by soaking, spraying or washing the carnivorous plant with glue traps which has been cultivated, by sucking or absorbing the glue onto fabric (particularly any type of paper, e.g. blotting paper), or by directly removing the glue from the carnivorous plant with glue traps which has been cultivated. In particular, in an advantageous embodiment, the carnivorous plant with glue traps is cultivated on a rigid system allowing a set of plants to be manipulated, turned over and their aerial parts soaked in a solution. Alternatively, the carnivorous plant with glue traps may be cultivated on an inclined plane covered with a material impermeable to water and the glue from the traps harvested by spraying and/or washing the aerial parts of the plant, the solution obtained being collected at the bottom of the inclined plane.

A second category of carnivorous plants which can be used in an advantageous embodiment of the process according to the invention is that of carnivorous plants possessing pitchers, trumpets or bladders.

The term "pitcher traps" means leaves ending in pitchers or ascidia, surmounted by a sort of cover called an operculum. The prey, attracted by nectar glands, enters the trap and slides on the inner walls which are surmounted by an impenetrable ring; the prey drowns in the liquid contained in the trap. Carnivorous plants with pitcher traps include notably the *Nepenthes* and *Cephalotus* genera.

The term "trumpet traps" is taken as meaning traps formed by leaves transformed into tubular trumpets. Insects attracted by nectar glands enter via an opening situated near the top of the trap. The inner wall of the latter is viscous or covered with downward pointing hairs preventing the prey climbing out and it ends by drowning as in the previous case. Carnivorous plants with trumpet traps include notably the *Sarracenia* genus.

The term "bladder traps" means traps composed of more or less transparent small pockets or bladders arranged along the length of the roots, with at one end an orifice surrounded by ramified hairs some of which control springing the trap when prey (often microscopic) brushes against them. The bladder fills suddenly ($\frac{1}{500}$ s.) sucking in both water and the prey. Then the bladder returns slowly to its original shape in about ½ hour by which time the prey no longer has any chance of escaping. Such traps are mainly found in species belonging to the genus *Utricularia*. Thus, advantageously the carnivorous plant with bladder traps used in the process according to the invention belongs to the genus *Utricularia*.

Advantageously, the carnivorous plant used has pitcher traps and is selected from the *Nepenthes* or *Cephalotus* genera.

In this case, as well as in the case of plants with trumpet traps, the digestive secretions in which the protein of interest is excreted form a liquid at the bottom of the pitcher or trumpet which can be harvested easily, either in sterile or non sterile conditions. Thus, when the carnivorous plant used in the process according to the invention has pitcher or trumpet traps, the protein of interest is advantageously obtained by harvesting the excreted fluids found inside the pitchers. This can be done for example in sterile conditions by sacrificing the pitchers or by using a device enabling puncture into said fluids inside the pitchers, such as a syringe or the like for instance. In non sterile conditions, the digestive secretions may for instance be collected from opened pitchers using a pipette or syringe or any suitable mean of collection.

The importance of pitcher traps, i.e. those with an operculum, is that the operculum is only opened by the plant at a certain stage in the trap's development. Before this stage, the operculum is closed, and the digestive secretions excreted into the trap are thus under sterile conditions. When using such plants, subject to harvesting the digestive secretions before the operculum opens and harvesting under sterile conditions, the recombinant protein produced by the carnivorous plant and excreted into the traps can be collected in a sterile form. Thus, advantageously, the carnivorous plant used in the process according to the invention has pitcher traps and is selected from the *Nepenthes* or *Cephalotus* genera. In this case, the fluids inside the pitchers are harvested advantageously therefore before the plant's pitchers open naturally. In particular, said fluids inside the pitchers can either be harvested by sacrificing the pitchers or by using a device enabling puncture into said fluids inside the pitchers under sterile conditions.

Whether pitcher or trumpet traps are concerned, the native proteases produced by the plant accumulate little by little at the bottom of the pitchers or trumpets. In order to limit the risks of degradation of the protein of interest by the digestive enzymes, the fluid inside the pitchers is harvested advantageously at a stage of the plant's development when the native proteases produced by the plant have not accumulated massively in said fluid. A person working in the field can determine simply for each type of plant the stage at which the quantity of protein of interest is at a maximum while the quantity of native proteases produced by the plant is still at a stage where it is limited.

When carnivorous plants with bladder traps are used in the process according to the invention, the protein is obtained advantageously by harvesting the fluid excreted inside the bladders. In particular, the fluid inside the bladders can be released by applying mechanical stress, such as combing, brushing, or stroking with filaments, or by ultrasound or even other sound waves being emitted onto the surface of the bladders.

DESCRIPTION OF THE DRAWINGS

FIG. 6. Observation of sticky droplets of glue after incubation with the X-Gluc substrate after absorption of the glue onto Whatman paper. A. Comparison of paper coated with glue droplets from GUS transformed *Drosera rotundifolia* (above), coated with glue droplets from control *Drosera rotundifolia* (untransformed wild plant, in the middle), or without droplets (bottom). B. Enlargement of A for the paper coated with glue droplets from GUS transformed *Drosera rotundifolia* (above), coated with glue droplets from control *Drosera rotundifolia* (untransformed wild plant, in the middle). C. Paper coated with droplets of glue from other GUS transformed *Drosera rotundifolia* plants. The dark grey areas correspond to blue areas indicating that the X-Gluc substrate has been transformed by the GUS enzyme, thus demonstrating the presence of the GUS enzyme in these areas.

EXAMPLES

Example 1

Transformation of *Drosera rotundifolia* Plants 1.1 Materials and Methods 1.1.1. Transformation of *Drosera rotundifolia* Plants with GFP or GUS Genes Drosera transformation was induced from the leaves, after wounding them and co-culturing them with *Agrobacterium tumefaciens* in order to carry out the transfer of the T-DNA to the plant cells, as described by Hirsikorpi et al. In our case, the transformation of the plants was performed with two distinct plasmidic constructions with different marker genes.

The T-DNA contained the NPTII gene coding for neomycin phosphotransferase II conferring resistance to kanamycin and:
- either the gene coding for GFP, Green Fluorescent Protein, from a jellyfish (*Aequorea victoria*), which fluoresces in the visible range when excited by UV light (395 nm),
- or the gene coding for the GUS enzyme, β-glucuronidase, which in the presence of X-Gluc substrate (5-bromo-4-chloro-3-indolyl-β-D-glucuronic acid) leads to the appearance of a blue colored product.

1.1.1 Observations of Leaves after Incubation with the X-Gluc Substrate

X-Gluc stock solution was diluted in X-Gluc buffer (100 mM Tris HCl, NaCl 50 mM, pH 7) to obtain a final concentration of 1 mM, and was applied directly to the plant parts. This was then left in the dark at 37° C. for 12 hours. The leaves were then soaked in an ethanol bath to eliminate the chlorophyll, and to reveal any blue staining caused by the possible presence of the GUS enzyme better.

Figure 1:
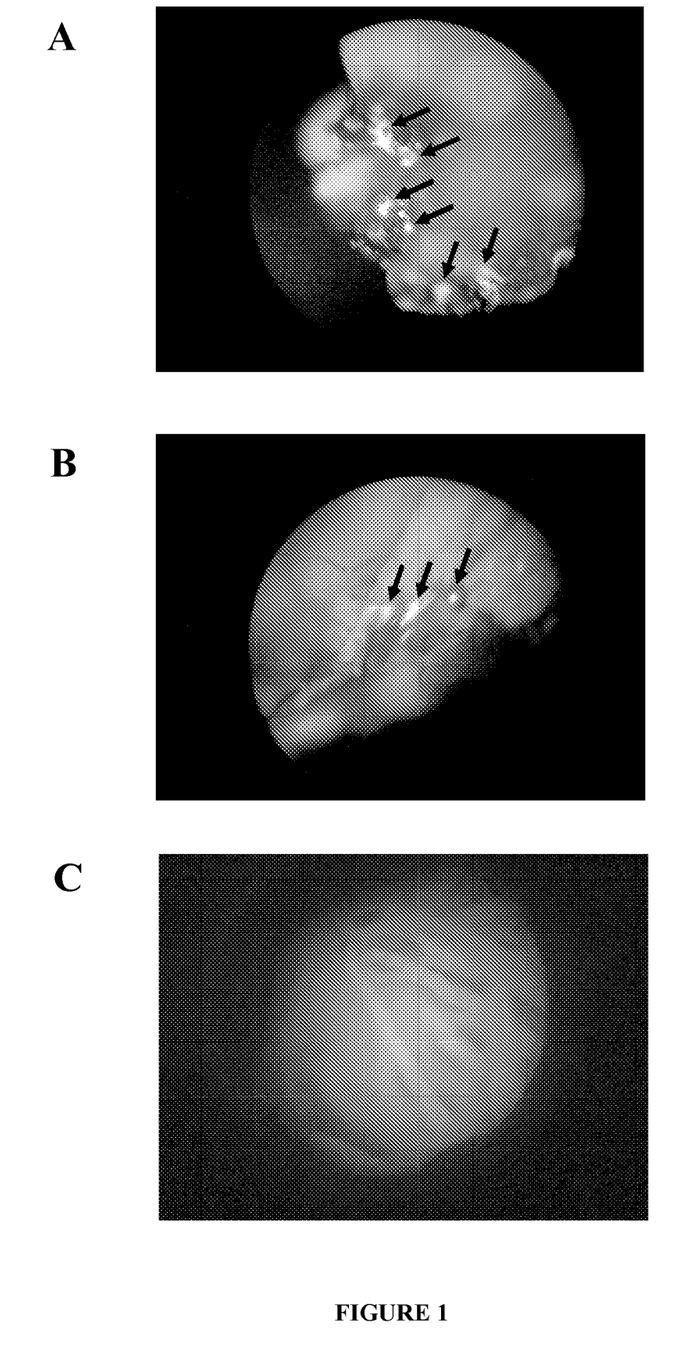
FIG. 1. Observation using a UV microscope of *Drosera rotundifolia* plants, GFP transformed (A and B) and control plants (C). The arrows indicate the site of areas of fluorescence (lightest areas) linked to the expression of GFP.

1.2 Results 1.2.1 GFP Transformed *Drosera rotundifolia* Plants 1.2.1.1 Observations of Leaves under a UV Microscope Leaf limbs from control and GFP transformed carnivorous plants were observed under the UV microscope. Certain GFP transformed leaves showed marked areas of fluorescence (FIGS. 1A and 1B, see arrows), while the leaves from control plants showed no fluorescence (FIG. 1C):

These observations under the microscope show that the plants had undergone GFP transformation and expressed the protein in the leaf limb.

1.2.1.2 Observations of Hairs and Mucilage under the UV Microscope

The search for fluorescence was then directed towards observation of glandular hairs on the leaves carrying glands secreting insect digesting enzymes and observation of droplets of glue or mucilage produced by these glands.

Figure 2:
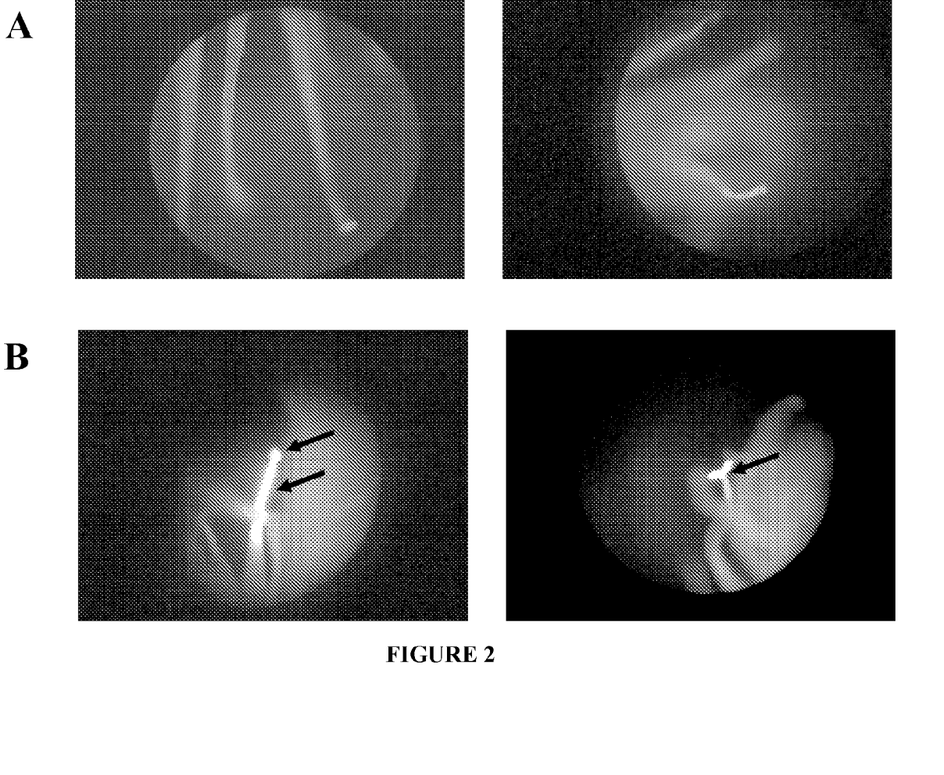
FIG. 2. Observation of glandular hairs present on the leaves of *Drosera rotundifolia* plants with glands secreting insect digesting enzymes—controls (untransformed wild plants, A) or GFP transformed plants (B). The arrows indicate the site of areas of fluorescence (lightest areas) linked to the expression of GFP.

On the control plants, the hairs observed in general showed no fluorescence (FIG. 2A). In spite of everything, certain observations did reveal the presence of fluorescence at the end of control hairs, but this was much less marked than that observed in certain hairs from GFP plants where the protein seemed to be expressed (FIG. 2B, see arrows).

1.2.1.3 Observations of Mucilage under the UV Microscope after Absorption onto Cigarette Paper In order to observe the possible presence of the GFP protein in the glue droplet, small squares of cigarette paper were cut out to sweep the leaves of control and GFP plants and absorb the glue onto the paper.

Figure 3:
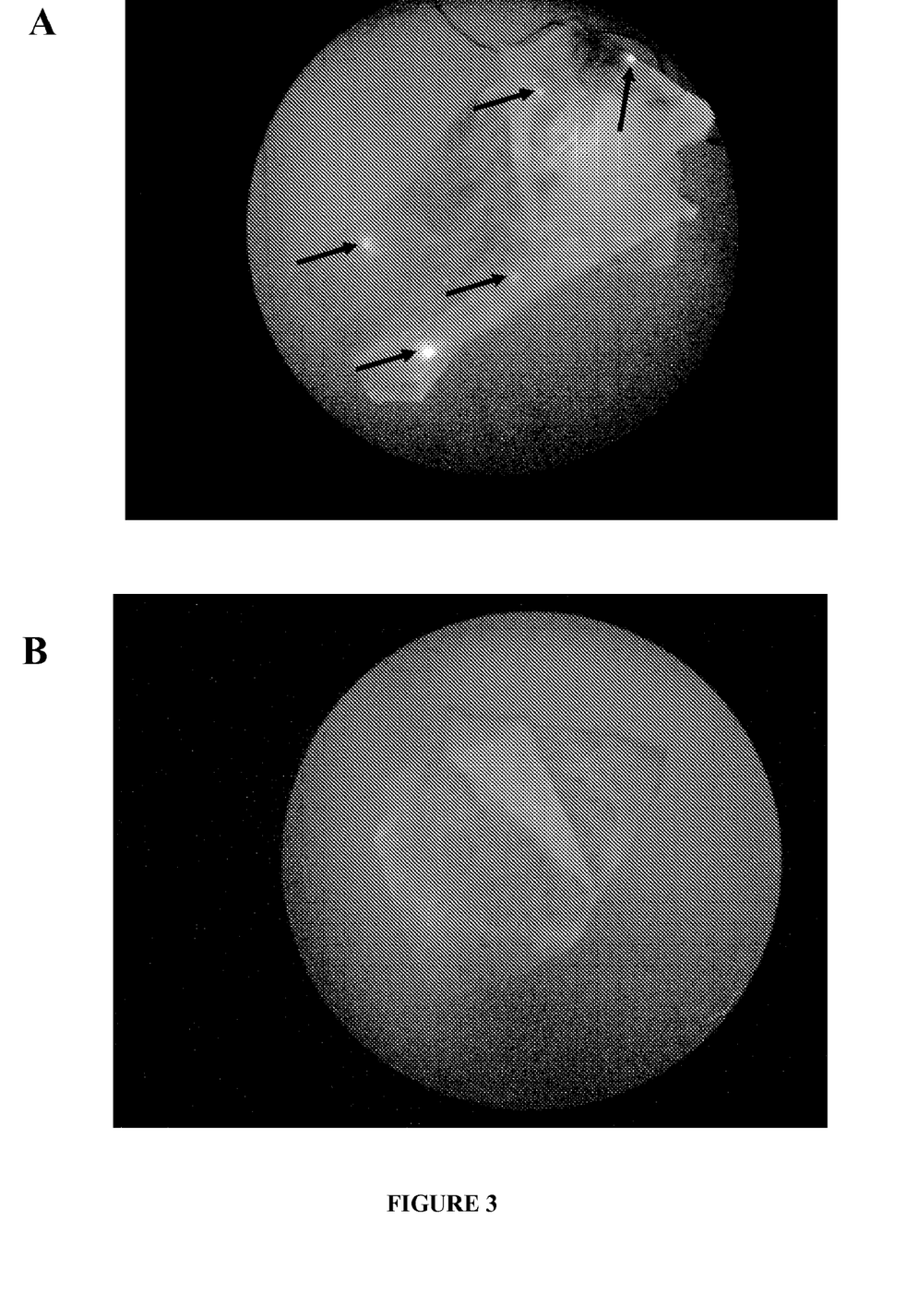
FIG. 3. Observation of mucilage from *Drosera rotundifolia* plants—GFP transformed (A) or control plants (untransformed wild plants, B) under a UV microscope after absorption onto cigarette paper. The arrows indicate the site of areas of fluorescence (lightest areas) linked to the expression of GFP.

The paper which had absorbed the droplets of mucilage from GFP plants was observed under the UV microscope: it had fluorescent spots (FIG. 3A, see arrows). The control paper showed none (FIG. 3B). This observation shows that the droplets of glue from GFP transformed plants expressed and contained the protein.

1.2.2 GUS Transformed *Drosera rotundifolia* Plants 1.2.2.1 Observations of Leaves after Incubation with the X-Gluc Substrate In order to verify that the plant had really been transformed, leaves from two supposedly transformed plants and control leaves were incubated with X-Gluc substrate.

Figure 4:
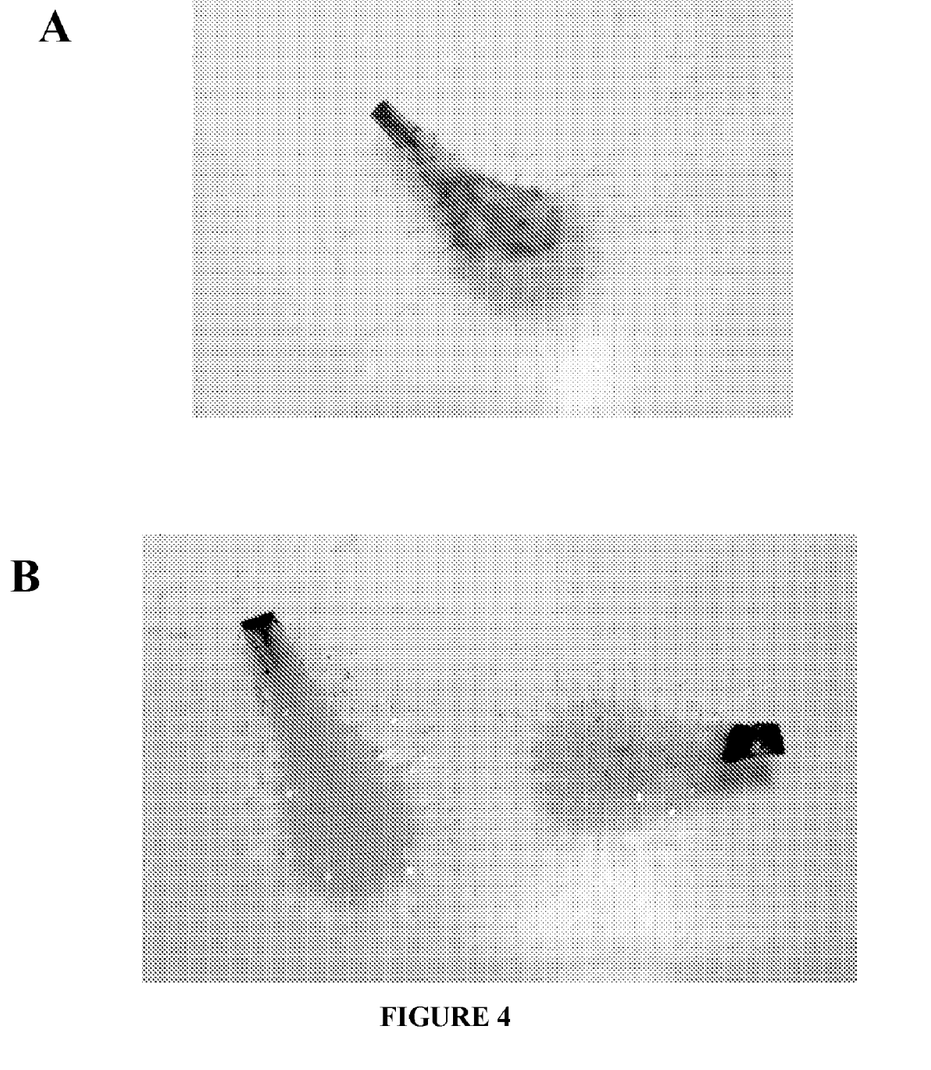
FIG. 4. Observation of leaves from *Drosera rotundifolia* plants—GUS transformed (A) or control plants (untransformed wild plants, B) after incubation with the X-Gluc substrate. The dark grey areas correspond to blue areas indicating that the X-Gluc substrate has been transformed by the GUS enzyme, thus demonstrating the presence of the GUS enzyme in these areas.

The supposed GUS leaves showed marked blue areas (FIG. 4A, see the dark grey areas) compared with the control leaves (FIG. 4B). It was thus deduced that the GUS enzyme was present and active in the supposed transformed plants, given the occurrence of this blue product formed in the presence of the substrate. It should be noted that the leaf is not entirely colored, certain areas remaining white. The control leaves showed blue areas where they had been injured or cuts had been made when separating the leaves from the plant, but the limb was not stained. (FIG. 4B).

1.2.2.2 Observations of Leaves after Incubation with X-Gluc Substrate Using a Binocular Microscope After incubation these control and GUS leaves were observed under the binocular microscope in order to see or exactly locate the blue staining.

Figure 5:
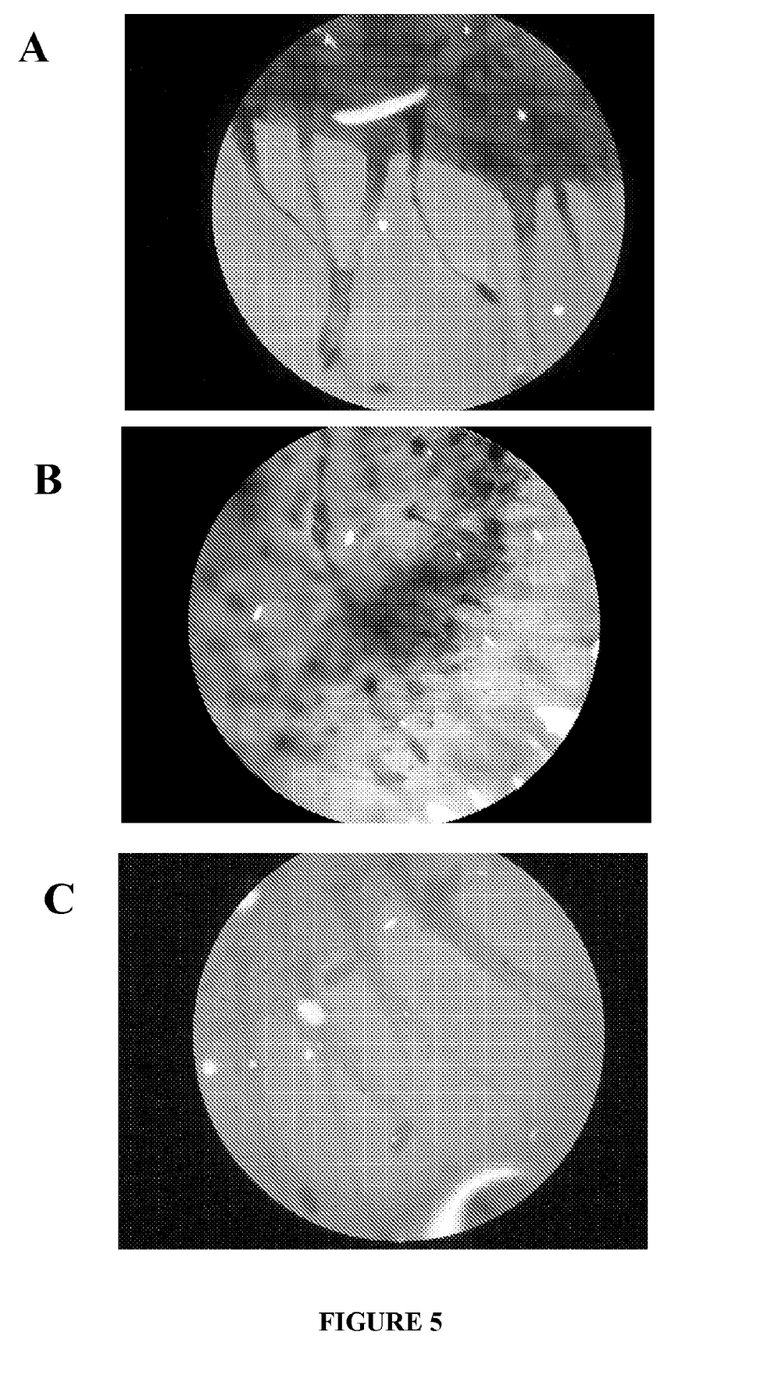
FIG. 5. Observation of leaves and hairs from *Drosera rotundifolia* plants—GUS transformed (A and B) or control plants (untransformed wild plants, C) after incubation with the X-Gluc substrate under a binocular microscope. The dark grey areas correspond to blue areas indicating that the X-Gluc substrate has been transformed by the GUS enzyme, thus demonstrating the presence of the GUS enzyme in these areas.

The leaves of GUS transformed plants (FIGS. 5A and 5B) showed staining only on the lower part of the hair (see dark grey staining). The end of the hair, the site of glue formation, was not colored. The hairs of leaves from control plants had no staining (FIG. 5C).

1.2.2.3 Observation of Droplets of Glue after Incubation with X-Gluc Substrate after Absorption of the Glue onto Whatman Paper As for the GFP plants, glue droplets from GUS and control plants were absorbed this time with Whatman paper (paper swept over the droplets to absorb as much as possible). These pieces of paper were then put to incubate in buffer and X-Gluc substrate for 12 hours at 37° C.

Figure 6:
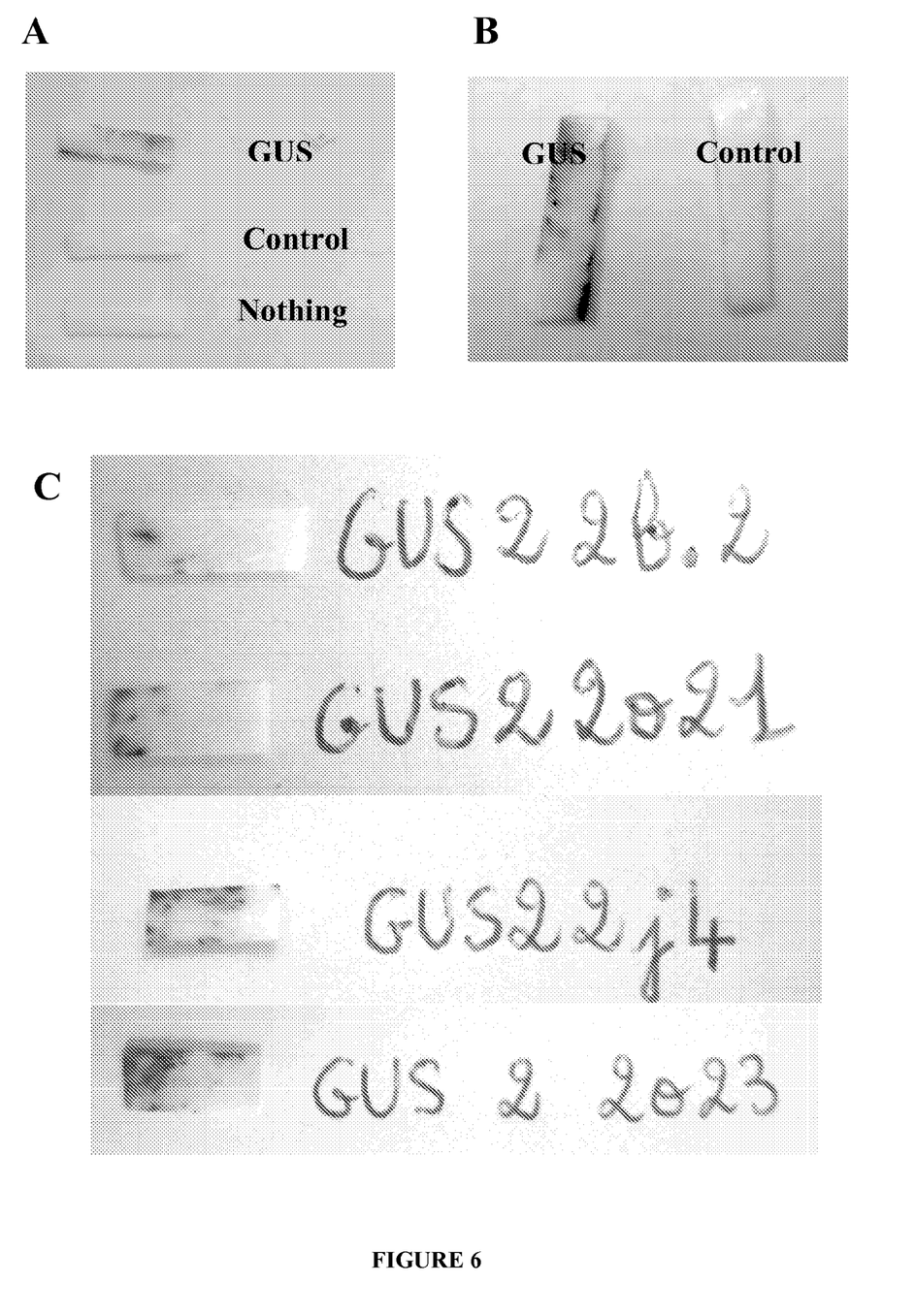

After 1 hour of incubation, the staining was already visible. Photos were taken after 12 hours of incubation (FIG. 6).

The paper with the droplets from GUS leaves (FIG. 6A above, and FIG. 6B left) have a blue stain (see dark grey areas) where the glue had been absorbed. The paper with the glue droplets from control leaves (FIG. 6A middle, and FIG. 6B right) show no staining, nor does the paper on which there is no glue (FIG. 6A bottom). The GUS enzyme is therefore expressed and present in the droplets of mucilage from leaves of GUS transformed plants but it not in those of control plants.

These experiments were reproduced on 17 GUS transformed plants, the transformation having been demonstrated by the blue staining of leaves after incubation with X-Gluc substrate. Of these 17 GUS transformed plants, 14 had droplets containing the GUS enzyme (paper spotted with blue). Only 3 apparently transformed plants did not seem to express the protein expected in the droplets. These results indicate therefore, that at least in the majority of cases, GUS transformed plants express the GUS enzyme and this is present in the mucilage droplets of the traps.

In addition, different intensities and quantities of blue were visible on the Whatman paper, suggesting that certain transformed plants express and secrete more or less GUS enzyme in the mucilage of the leaves. In order to confirm this, tests were carried out on droplets from a single leaf of GUS plants: 5 leaves from 5 GUS plants already previously tested were taken, and the droplets from each leaf were absorbed separately onto a Whatman paper. The results obtained to date confirm that GUS transformed plants express and secrete more or less of the GUS protein in the mucilage droplets.

1.2.2.4 PCR Analysis of the Insertion of the Expression Vector into the Genome of Transformed Plants The plants were transformed using 2 genes, which occur on the same T-DNA fragment: the GUS gene and a kanamycin resistance gene (NPTII), which permits plant selection by adding the antibiotic to the culture medium. Indeed, if the plant has incorporated the kanamycin resistance gene, it survives in the medium containing kanamycin, while untransformed plants die, so that transformed plants are selected.

Both the GUS and NPTII genes were integrated simultaneously into the plant's genome. Thus the presence in the plant's genome of the NPTII gene indicates the presence in the plant's genome of the GUS gene, demonstrating transformation of the plant.

For technical reasons concerning PCR, the presence of the NPTII gene in the genome of the plant was detected by PCR amplification of a fragment of the NPTII gene in 2 plants in which enzyme tests had already indicated the presence of the GUS gene.

Figure 7:
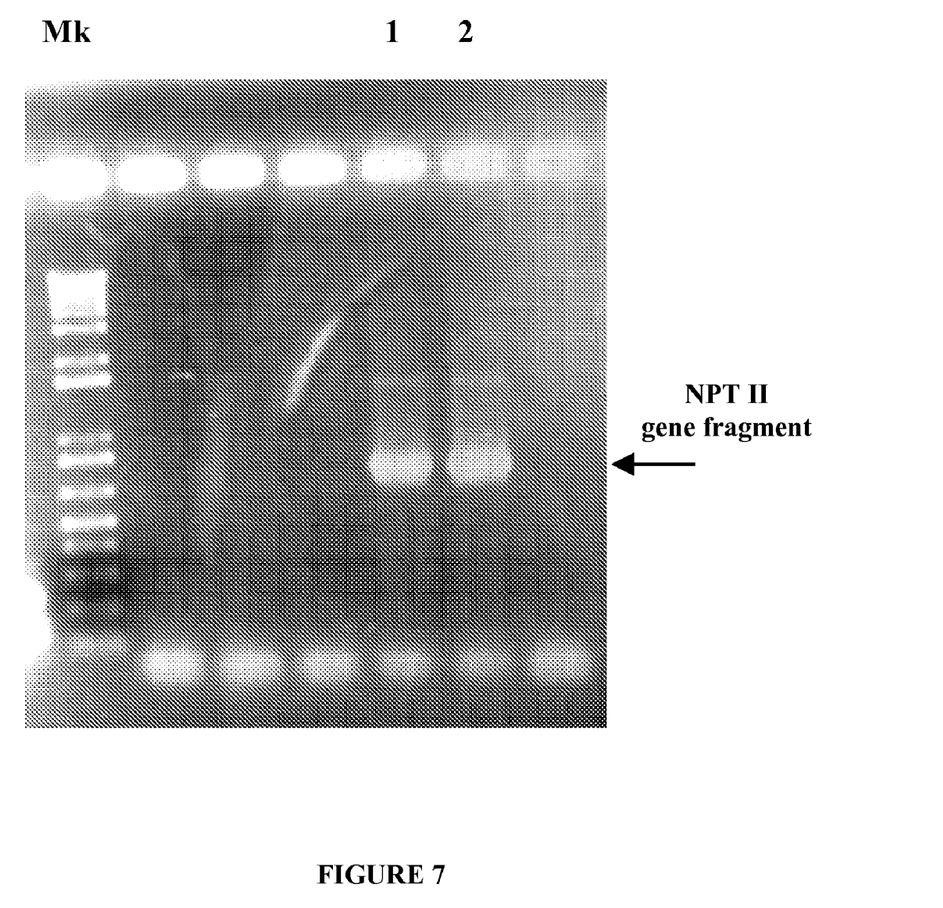
FIG. 7. PCR analysis of the insertion of the expression vector containing the GUS and NPTII genes in the genome of transformed plants, by detection of the NPTII gene. Mk: size markers. 1 and 2: plants tested.

The results are given in FIG. 7, and show that the fragment of the NPTII gene had been amplified by PCR in these 2 plants, thus demonstrating the insertion into the plant's genome of the expression vector including the GUS and NPTII genes.

1.3 Conclusion

The results given above clearly indicate that it is possible to generate a genetically modified carnivorous plant in which the gene of a protein of interest has been inserted, and to harvest the protein of interest easily from the digestive secretions of traps excreted by the plant (here, from the glue).

In addition, the tests carried out on the two proteins of interest used (GUS and GFP) indicate that the proteins obtained are functional, despite the existence of digestive enzymes.

REFERENCES

1. Ullah, A. H. J., Sethumadhavan, K., Mullaney, E. J., Ziegelhoffer, T., and Austin-Phillips, S. (2003). Fungal phyA gène expressed in potato leaves produces active and stable phytase. *Biochemical and Biophysical Research Communications* 306(2). 603-609.
2. Gao, Y., Suo, G. L., Han, J., He, Z. Q., Yao, W., Dai, J. W. (2006). Expression of Human BMP-2 Gène in Différent Tissues of Tobacco Plants. Acta Genetica Sinica 33 (1), 56-62.
3. Gallie, D. R., and Chang, S. C. (1997). Signal transduction in the carnivorous plant Sarracenia purpurea—Régulation of secretory hydrolase expression during development and in response to resources. Plant Physiology 115, 1461-1471.
4. Matusikova, L, Salaj, J., Moravcikova, J., Mlynarova, L., Nap, J. P., and Libantova, J. (2005). Tentacles of in vitro-grown round-leaf sundew (*Drosera rotundifolia L.*) show induction of chitinase activity upon mimicking the présence of prey. Planta 222, 1020-1027.
5. EP0019808
6. WO 99/42115
7. WO 02/057408
8. Hirsikorpi M., Kàmàràinen. T., Teeri. T., Hohtola. A. (2002). Agrobacterium-mediated transformation of round leaved sundew (*Drosera rotundifolia L.*). Plant Science, 162, 537-542.
9. Schweikert, R. J., Beaudoin, S. E., and Owen, T. P. (2006). Induced changes to the ultrastructure of the digestive glands from the carnivorous pitcher plant *Nepenthes alata*. In "Plant Biology 2006" (A. S. o. P. Biologists, éd.). Unpublished, Boston, Mass., USA.
10. Chikwamba, R. K., Scott, M. P., Mejia, L. B., Mason, H. S., and Wang, K. (2003). Localization of a bacterial protein in starch granules of transgenic maize kernels. Proceedings of the National Academy of Sciences of the United States of America 100, 11127-11132.
11. Juniper, B. E., Robins, R. J., Joël, D. (1989) The Carnivorous Plants. Londres, Académie Press, 353 p.
12. Burch-Smith, T. M., Anderson, J. C, Martin, G. B., and Dinesh-Kumar, S. P. (2004). Applications and advantages of virus-induced gène silencing for gène function studies in plants. Plant Journal 39, 734-746.

13. Deblock, M. (1993). The Cell Biology of Plant Transformation—Current State, Problems, Prospects and the Implications for the Plant-Breeding. Euphytica71, 1-14.
14. Voinnet, O. (2005). Induction and suppression of RNA silencing: Insights from viral infections. Nature Reviews Genetics 6, 206-U1.
15. Frazier, C. K. (2000) The enduring Controversies Concerning the Process of Protein Digestion in *Nepenthes* (Nepenthaceae). International carnivorous plant Society 29(2), 56-61
16. Lobareva L S. Rudenskaia G N. Stepanov V M.
17. Takahashi, K., Chang, W., Ko, J. (1974). Specific inhibition of acid proteases from brain, kidney, skeletal muscle, and insectivorous plants by diazoacetyl-DL-norleucine methyl ester and by pepstatin. The Journal of Biochemistry 76(4), 897-900.
18. Pratelli, R., Sutter, J.-U., and Blatt, M. R. (2004). A new catch in the SNARE. Trends in Plant Science 9, 187-195.
19. Nicchitta, C. V. (2002). A platform for compartmentalized protein synthesis: protein translation and translocation in the ER. Current Opinion in Cell Biology 14, 412-416.

The invention claimed is:

1. Process for producing at least one protein, comprising the cultivation of a carnivorous plant, wherein said plant has been genetically modified to express said protein or proteins, and collecting said protein or proteins from the digestive secretions of the traps of said carnivorous plant.

2. Process according to claim 1, wherein said protein or proteins are expressed in the plant cell and secreted by the plant's native secreting system.

3. Process according to claim 1, wherein said plant has been genetically modified by transformation by Agrobacterium, biolistics, electroporation, microinjection or the use of viral vectors.

4. Process according to claim 1, wherein said protein is selected from a medicinal product for veterinary or human use, a cosmetic agent, a phytopharmaceutical agent, a diagnostic agent, a nutraceutical agent or a laboratory reagent.

5. Process according to claim 1, wherein said plant is subjected to chemical and optionally mechanical stimuli mimicking the capture of a prey and inducing activation of the system producing and secreting proteins by said plant into traps.

6. Process according to claim 1, wherein, said plant is cultivated in the absence of any chemical and/or mechanical stimulus mimicking the capture of a prey and inducing activation of the system producing and secreting proteins by said plant into traps.

7. Process according to claim 1, further comprising the inhibition of the synthesis of one or more digestive enzymes by said carnivorous plant.

8. Process according to claim 7, wherein at least one of said digestive enzymes the synthesis of which is inhibited is a protease.

9. Process according to claim 7, wherein the inhibition of the synthesis of one or more digestive enzymes by said carnivorous plant is carried out by genetic technologies selected from deletion from the plant's genome of at least one digestive enzyme gene, switching off the transcription of at least one digestive enzyme gene by silencing, and/or ectopic expression of at least one digestive enzyme inhibitor gene.

10. Process according to claim 7, wherein the inhibition of the synthesis of one or more digestive enzymes by said carnivorous plant is performed by directly adding a solution inhibiting the digestive enzyme or enzymes to the digestive liquid of the traps, or by controlling the pH and/or temperature conditions of the digestive liquid.

11. Process according to claim 1, wherein said protein comprises a peptide signal sequence permitting its transport into the endoplasmic reticulum.

12. Process according to claim 1, wherein said carnivorous plant is further genetically modified to express at least one gene encoding a protein including at least one SNARE type domain.

13. Process according to claim 1, wherein said carnivorous plant has glue traps.

14. Process according to claim 13, wherein said carnivorous plant having glue traps is selected from the *Drosera, Pinguicula, Byblis, Drosophyllum*, and *Triphyophyllum* genera.

15. Process according to claim 13, wherein said protein is obtained by harvesting the glue from the traps by soaking, spraying or washing of said plant, by suction or absorption onto fabric of the glue of said plant, or by direct collection of the glue.

16. Process according to claim 15, wherein said plant is cultivated on a rigid system allowing a set of plants to be manipulated, turned over and their aerial parts soaked in a solution.

17. Process according to claim 15, wherein said plant is cultivated on an inclined plane covered with a material impermeable to water, the glue from the traps being harvested by spraying and/or washing the aerial parts of the plant and the solution obtained being collected at the bottom of the inclined plane.

18. Process according to claim 1, wherein said carnivorous plant has pitcher, trumpet or bladder traps.

19. Process according to claim 18, wherein said protein is obtained by harvesting the secreted fluids found inside the pitchers, trumpets, or bladders.

20. Process according to claim 18, wherein said carnivorous plant having pitcher traps is selected from the *Nepenthes* or *Cephalotus* genera.

21. Process according to claim 19 wherein said fluids found inside the pitchers are harvested before the pitchers of said plant open naturally.

22. Process according to claim 21, wherein said fluids inside the pitchers are harvested by sacrificing the pitchers or by using a device allowing puncture into said fluids inside the pitchers under sterile conditions.

23. Process according to claim 19, wherein said fluids inside the pitchers are harvested at a stage of the plant's development when the quantity of native proteases produced by the plant is still at a stage where it is limited.

\* \* \* \* \*